United States Patent [19]

Trestianu et al.

[11] Patent Number: 4,734,107

[45] Date of Patent: Mar. 29, 1988

[54] METHOD AND DEVICE FOR THE DIRECT ON-COLUMN INJECTION OF SAMPLES CONTAINING HIGH BOILING POINT AND/OR MEDIUM VOLATILE COMPOUNDS

[75] Inventors: Sorin Trestianu, Bruxelles, Belgium; Fausto Munari, Milan, Italy; Giovanni Ostan, Milan, Italy; Carlo Saravalle, Milan, Italy

[73] Assignee: Carlo Erba Strumentazione S.p.A., Milan, Italy

[21] Appl. No.: 817,195

[22] Filed: Jan. 8, 1986

[30] Foreign Application Priority Data

Feb. 21, 1985 [IT] Italy .................................. 19601 A/85

[51] Int. Cl.$^4$ ............................................... B01D 15/08
[52] U.S. Cl. .......................................... 55/67; 55/197; 55/208; 55/386
[58] Field of Search ........................ 55/67, 197, 386

[56] References Cited

U.S. PATENT DOCUMENTS

| | | | |
|---|---|---|---|
| 4,269,608 | 5/1981 | Sisti et al. | 55/67 |
| 4,383,839 | 5/1983 | Sisti et al. | 55/67 |
| 4,405,344 | 9/1983 | Sisti et al. | 55/67 |
| 4,559,063 | 12/1985 | Munari et al. | 55/67 |

*Primary Examiner*—Robert Spitzer
*Attorney, Agent, or Firm*—Millen & White

[57] ABSTRACT

The invention relates to a method and device for direct non-vaporizing on column-injection of samples containing high boiling point and/or medium volatile compounds, in gas chromatographic analysis on capillary column. For reasons of economy, the oven containing the column is maintained at a temperature very mcuh higher than the boiling point of the solvent, while the initial part of the column (at least 10 cm) is cooled during the injection. The quantity of sample and solvent injected is related to the length of the cooled section of the column.

21 Claims, 6 Drawing Figures

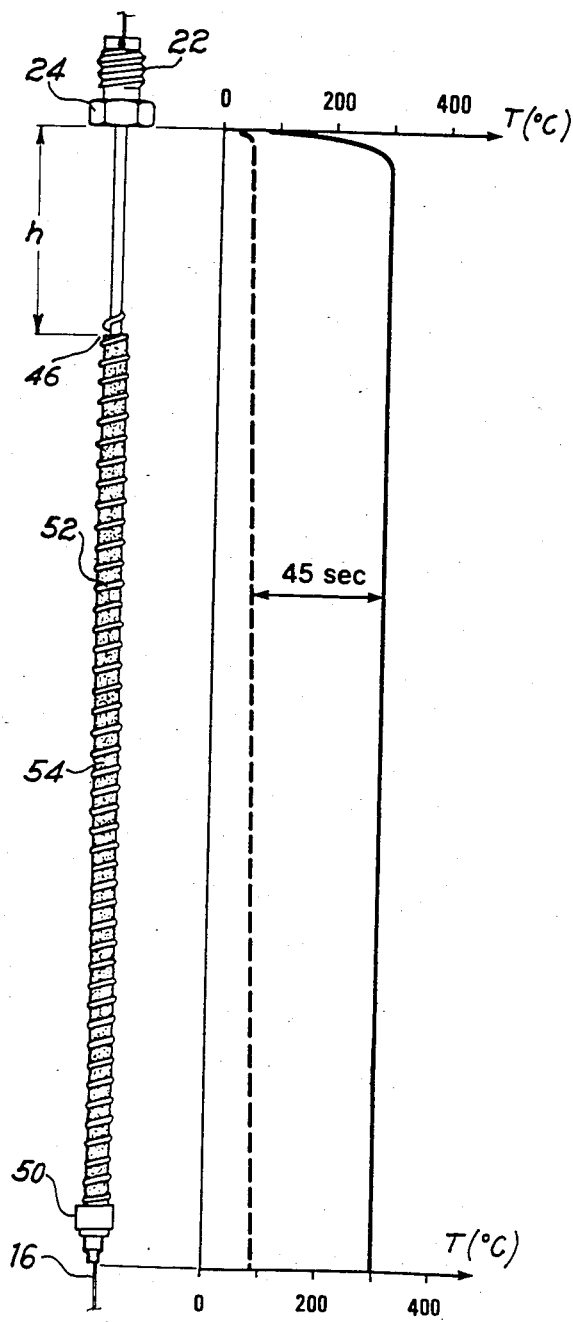
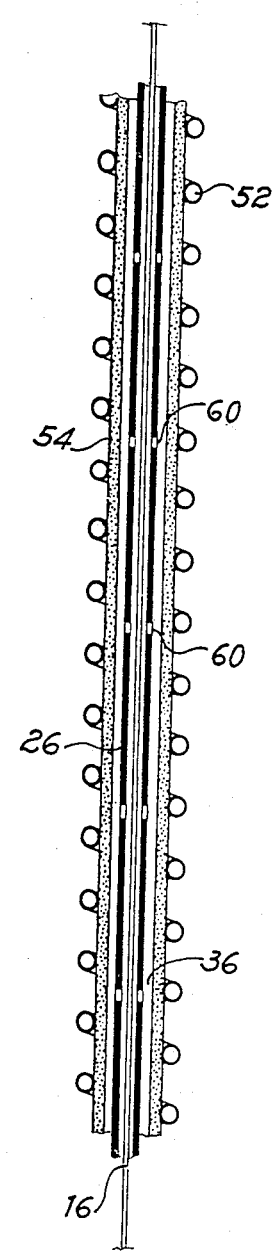
Fig. 3
Fig. 4

METHOD AND DEVICE FOR THE DIRECT ON-COLUMN INJECTION OF SAMPLES CONTAINING HIGH BOILING POINT AND/OR MEDIUM VOLATILE COMPOUNDS

BACKGROUND OF THE INVENTION

1. Field of the Invention

The present invention relates to a method and device for direct non vaporizing on-column injection of samples containing high-boiling point and/or medium volatile compounds in gas chromatographic analysis on capillary columns.

2. Description of the Prior Art

Gas chromatography using a capillary column operates in accordance with well known principles, using an apparatus also well known, consisting essentially of an oven or gas chromatography chamber containing the capillary column; an injector device at the upstream end of the column and a detector device at the downstream end. The sample is diluted in an appropriate solvent and admitted to the column through the injector. It is carried through the column by the carrier gas. The elution of the sample occurs according to a time parameter based principally on the affinity of the sample for the stationary phase, which coats the inside of the column, and the speed of the carrier.

A method of direct non vaporizing injection, known as "on column", is reported in U.S. Pat. No. 4,269,608. According to this method, the sample is injected directly into the column, either into the upstream section of the column or into a section of the column, free of stationary phase, connected to the upstream end of the column. The technique requires the sample to be injected while the oven temperature is maintained below the boiling point of the solvent (Sbp). The use of oven temperatures below the boiling point of the solvent, besides needlessly prolonging the analysis, leads to deterioration in the chromatographic peaks, and therefore, deterioration in the results. Further, the use of temperatures much higher than the solvent boiling point might lead to an "explosive" expansion of the solvent in the column, with loss of sample and discrimination such as to render the analysis unreliable. Also, for reasons connected with the preparation of the sample, the solvents used have boiling points lower than 100° C., and therefore, the oven temperatures during injection must be kept very low. The on-column injection method patented by the Applicant (U.S. Pat. No. 4,269,608) allows the sample to be injected at oven temperatures 15°–30° C. above the boiling point of the solvent, eliminating the deformation of the chromatographic peaks, which improves the results. In the embodiment described in the patent, there was a system of secondary cooling, which did not allow injection at oven temperatures very much greater than Sbp.

In the same patent, the Applicant offered a solution to this type of problem: moving the injector and the injection section of the column outside the oven during injection, and returning it after the solvent had passed through the column. The main defect of this solution is that it requires mechanical movement of the injector and column, which, among other things, is difficult to automate.

When the sample contains high boiling point and/or medium volatile compounds and the analysis is specifically for them, the injection at oven temperatures low with respect to the initial temperature required for the chromatographic separation creates needless time losses in heating the oven and cooling after the "temperature program" (the analysis is usually made by programming the oven temperature between an initial and final temperature).

OBJECTS OF THE INVENTION

With the above premises, the present invention relates to a new method and new device for the direct non-vaporizing on-column injection of samples containing high boiling point and/or medium volatile compounds dissolved in volatile solvents, which allow oven temperatures at the injection stage to be much higher than those in the "on-column" technique.

SUMMARY OF THE INVENTION

Essentially the direct on-column injection method according to the invention is characterized by:

(a) oven temperature during the injection phase being maintained at an above Sbp+50° C. where Sbp is the solvent boiling point;

(b) the solvent and sample being injected into a part of the column or precolumn located in the oven and cooled during the injection stage by a cooling device;

(c) the maximum quantity of sample and solvent injected being related to the length of the column or precolumn being cooled downstream of the point of injection;

(d) the cooling device being disengaged when the solvent has passed the said cooled part of the column or precolumn.

In particular, the cooling device is adjusted to bring the temperature of the cooled part of the column or precolumn to that corresponding to the requirements of the direct non-vaporizing on-column injection. In other words, to a temperature sufficiently low to keep all the high boiling point and/or medium volatile compounds to be analysed in the cooled tract of the column or precolumn. To this end, the cooled tract of the column is at least 10 cm long and the maximum quantity of sample and solvent injected is related to this length, as well as to the diameter of the column and the type of solvent, so that the area of the initial tract wetted by the sample on injection is not greater than the length cooled, e.g. this quantity could be in the order of 0.1–0.2 $\mu$l/cm of cooled column in normal operating conditions.

At the end of the injection, the shutting off of the cooling device causes rapid heating of the aforementioned tract until it reaches oven temperature.

To carry out this process, the invention provides for an injection device of the direct non-vaporizing on-column type, e.g. as described in U.S. Pat. No. 4,269,608 and incorporating a cooling system which can be switched on and off and which extends for at least 10 cm along the initial tract of the gas chromatographic column or precolumn located in the oven.

Where the injector, in the case of the U.S. patent referred to, had a secondary cooling device worked by gas (e.g. air) fed from outside and passing along an initial tract of the column inside the oven, now the cooling means according to the invention is a tube surrounding the initial tract of the column for at least 10 cm and open to the oven at the downstream end and connected at the upstream end to a source of coolant gas, whose temperature and/or pressure and/or flow can be controlled. It would be convenient if this tube, which should be quickly and easily detachable and reattachable to the body of the injector, were of a high thermal conductivity material so that the tract of the column involved in the cooling could follow correctly the heating program of the oven when the cooling is switched off.

In the attached drawings, an embodiment of the injection device according to the invention is illustrated, derived from that described in example in the U.S. Pat. No. 4,269,608 in the name of the same Applicant.

BRIEF DESCRIPTION OF THE DRAWINGS

In the drawings:

FIG. 3 is a side view of the cooling tube particularly suited to the invention, and also shows the results of temperature measurements made.

FIG. 4 is an enlarged cross-section of part of the tube shown in FIG. 3.

DESCRIPTION OF THE PREFERRED EMBODIMENT

Figure 1:
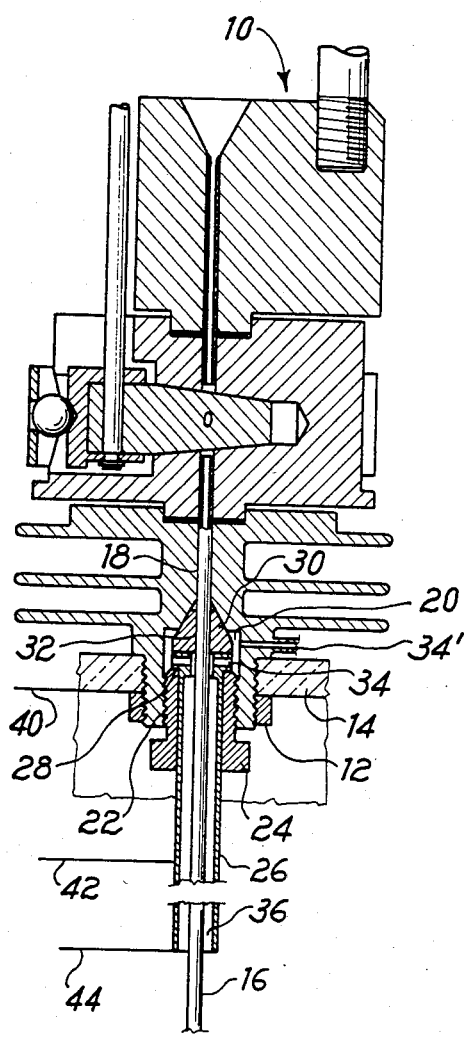
FIG. 1 is an axial section of an injector fitted with the device according to the invention.
Figure 2:
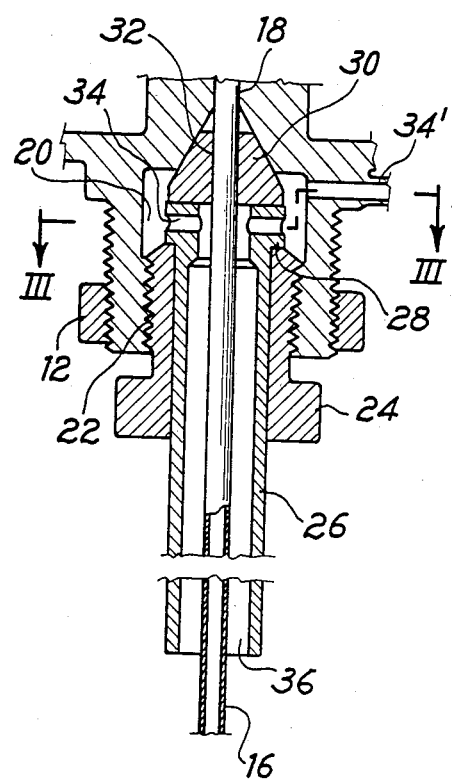
FIG. 2 shows in larger scale a detail of the device shown in FIG. 1.

In the drawings a gas chromatographic injector of the already known "on-column" type is shown in axial section and indicated as 10. The injector, which shall not be described in detail since this has already been done in U.S. Pat. No. 4,269,608, is attached by the retaining nut 12 to the oven body 14 in which the gas chromatography column is located. The injector 10 presents a precision drilled internal seating 18, which leads into a lower chamber 20 opening into the oven. This seating 18 takes the end of the gas chromatography column or precolumn free of stationary phase connected downstream to the gas chromatography column. The chamber 20 has a threaded section 22 to take the retaining barrel 24 which holds the tube 26 whose head 28 abutts against a conical gland 30 making a gas tight seal (under the action of tightening the barrel 24) with the countersunk opening connecting the seating 18 with the chamber 20. The conical gland 30 has an opening 32 for the conical 16, while the head 28 has a distribution chamber surrounding the end of the column or precolumn 16 and connected via a duct 34 to the chamber 20 which in turn is connected to the outside by the opening 34'. The distribution chamber 28 is connected to the space 36 between the exterior of the column or precolumn 16 and the interior of the tube 26, whose diameters are therefore different, and ultimately opens to the interior of the oven 14. As illustrated, the tube 26, and therefore the space 36, extend coaxially with the column or precolumn 16, inside the oven for a certain length which determines the length of the column or precolumn which is cooled during the injection of the sample.

A fluid (possibly, but not necessarily, compressed air) enters through the ducts 34, 34'. This fluid, guided by the tube 26, runs through the space 36 and washes over the exterior of the column or precolumn.

For the analysis of high boiling point and/or medium volatile compounds the tube 26 should preferably be of high thermal conductivity material and extend into the oven (whose inner wall 40 is shown) for at least 10 cm beyond the point of injection, e.g. the point of injection 42 is shown and the tube 26 extends as far as point 44.

The injection is carried out with the oven temperature much higher than the boiling point of the solvent while compressed air is passed through space 36, maintaining that part of the column or precolumn to the point 44 at a temperature much lower than the oven. While the solvent is vapourized and passes into the column, the high boiling point and/or medium volatile components remain in the initial tract of the column or precolumn 16 up to the point 44 because of the thermal conditions and, if the column is coated, because of the affinity of the compounds for the stationary phase.

At this point, the cooling is switched off so that the initial tract of the column or precolumn 16 can reach oven temperature and begin elution of the sample, following the changes in temperature programmed.

A type of tube preferred for conducting cooling air is shown in FIGS. 3 and 4.

As can be seen, the tube consists of a threaded connection 22 at the top of the locking barrel 24 for locating it in the non-vaporizing direct on-column injector, and the tube 26 proper below. From the point 46, a certain distance "h" below the locking nut 24 the tube is enclosed by a jacket 54 of a material (e.g. glass fibre) porous to the coolant gas (e.g. air). The jacket is held in position by a lower retaining ring 50 and a spiral wire 52 wrapped around its length, allowing the jacket to expand radially.

The tube 26 has a restriction in the end which opens into the oven, formed by narrowing the tube, to create a counterpressure in the space 36. The tube 26 has a series of radial holes 60, through which the air, forced in through the connection 22 and impeded by the restriction, passes to form an air space between the tube 26 and the jacket 54 as shown in FIG. 4. In such conditions, the air space acts as a temporary insulation and helps to maintain the lower temperature in the space 36 and the corresponding tract of the column 16. When the cooling is discontinued, the jacket 54 returns to its position around the tube 26 under the action of the spiral retainer 52, eliminating the air space and its insulation, and allowing the tube 26, the space 36 and the enclosed tract of column or precolumn 16 to reach oven temperature quickly. The initial tract of tube 26 of length "h" is not jacketed because it is already sufficiently cooled by the efficiency of the initial secondary cooling as well as the primary cooling of the injector.

In FIG. 3, beside the tube diagram are shown:

(a) Broken Line: temperature profile with the oven at 300° C. and cooling air entering at a pressure of 3 kg/cm$^2$ and the oven at 300° C.

(b) Solid Line: temperature profile after cooling is stopped. The time taken to go from curve (a) to curve (b) is 45 secs.

In an embodiment of the invention, 0.5 μl of colza oil sterols dissolved in heptane were injected on a 20 m OV 17 column of internal diameter 0.32 mm and stationary phase thickness of 0.15 μm.

Figure 5:
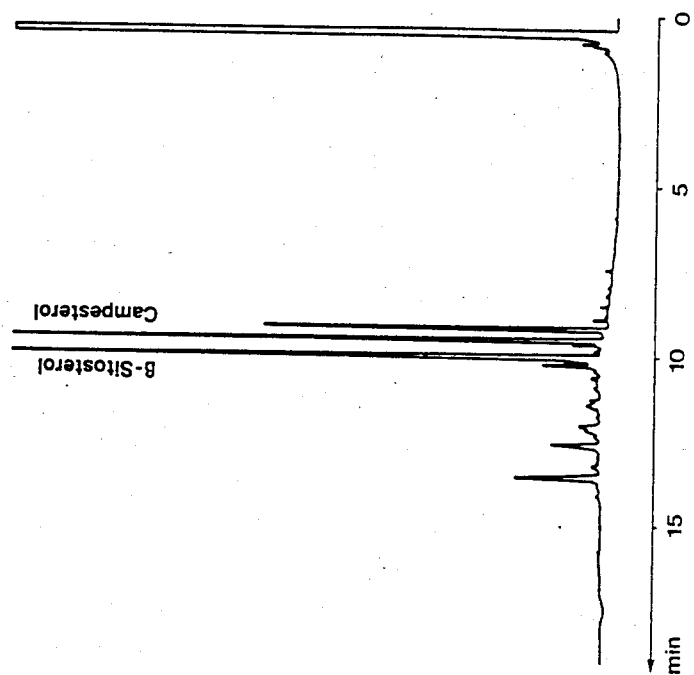
FIGS. 5 and 6 are chromatograms for comparison—the first made according to current practice and the second according to the invention.
Figure 6:
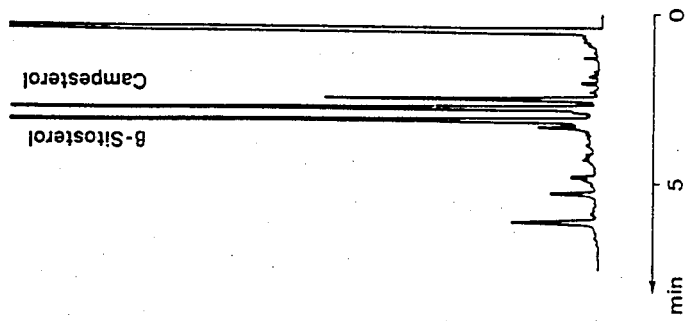

Cooling was by compressed air at 3 kg/cm$^2$ using the cooling tube shown in FIG. 3, with an overall length, from the roof of the chamber of 18.6 cm. Two analyses were made of the same sample, the first starting with the oven at 90° C. and rising at 300° C. with a temperature gradient of 30° C./minute, and thereafter proceding isothermically. The result is shown in FIG. 5 with the time plotted on the horizontal axis. The second analysis was made by injecting the sample with the oven temperature at 300° C. and maintaining this for the time required for the analysis. The results are shown in FIG. 6, giving results identical to FIG. 5, but in much shorter time.

The method and device described in the invention can be used with any type of capillary column and with samples containing volatile components, provided that these volatile components are not required to be analysed.

We claim:

1. A method for the direct non-vaporizing on-column injection of samples containing high boiling point and/or medium volatile components dissolved in volatile solvents, by means of an apparatus for gas chromatographic analysis comprising an oven which houses a gas chromatography column whose upstream end is fitted directly, or by a precolumn, to a non-vaporizing direct on-column injector, the method characterized in that:
   (a) the oven temperature is maintained at least 50° C. above the solvent boiling point;
   (b) the sample and solvent are injected at a point along a tract of the column, or precolumn, within the oven while being cooled by a cooling system in operation during injection wherein the cooling system maintains the tract of the column or precolumn at a temperature sufficiently low to maintain therein the high boiling point and/or medium volatile compounds to be analyzed, and wherein the tract of the column or precolumn is cooled for at least 10 cm along the length thereof.

2. A method according to claim 1, wherein the quantity of sample injected is in the order of 0.1–0.2 $\mu$l per cm. of cooled section of column or precolumn.

3. A device for the realization of the method of claim 2, consisting of a non-vaporizing, direct on-column injector, where the injector is fitted with a detachable means of cooling extending along a section of the gas chromatography column or precolumn inside the oven for at least 10 cm.

4. An injector device according to claim 3, of a type having secondary cooling by means of a gas fed from an outside source and run along an initial tract of the column or precolumn within the oven, characterized in that it comprises a tube surrounding an initial section of the column or precolumn for at least 10 cm, which is open to the oven at its downstream end and is connected to a controlled source of coolant gas at its upstream end.

5. An injector device according to claim 4, where the tube is made of high thermal conductivity material.

6. An injector device according to claim 4, where the tube is mounted detachably in the body of the direct on-column injector.

7. An injector device according to claim 4, where the tube has a number of radial holes and is covered, at least in the area of the holes, by a flexible cover to create a gas space outside the tube during the cooling.

8. An injector device according to claim 7, where the tube has an internal constriction downstream of the holes.

9. An injector device according to claim 7, where the flexible cover comprises a glass fibre jacket and an elastic external winding.

10. A method according to claim 1, wherein the tract of column or precolumn is cooled for at least 10 cm.

11. A method according to claim 10, wherein the quantity of sample injected is in the order of 0.1–0.2 $\mu$l per cm of cooled section of column or precolumn.

12. A device for the realization of the method of claim 11 consisting of a non-vaporizing direct on-column injector, where the injector is fitted with a detachable means of cooling, extending along a section of the gas chromatography column or precolumn inside the oven for at least 10 cm.

13. A device for the realization of the method of claim 1, consisting of a non-vaporizing direct on-column injector, where the injector is fitted with a detachable means of cooling, extending along a section of the gas chromatography column or precolumn inside the oven for at least 10 cm.

14. An injector device according to claim 13, of a type having a secondary cooling by means of a gas fed from an outside source and run along an initial tract of column or precolumn within the oven, characterized in that it comprises a tube surrounding an initial section of the column or precolumn for at least 10 cm, which is open to the oven at its downstream end and is connected to a controlled source of coolant gas at its upstream end.

15. An injector device according to claim 14, where the tube is of high thermal conductivity material.

16. An injector device according to claim 15, where the tube is mounted detachably in the body of the direct on-column injector.

17. An injector device according to claim 16, where the tube has a number of radial holes and is covered, at least in the area of the holes, by a flexible cover to create a gas space outside the tube during the cooling.

18. An injector device according to claim 17, where the tube has an internal construction downstream of the holes in the sense of the coolant gas direction.

19. A method of injecting directly non-vaporizing samples dissolved in a solvent into a gas chromatography column by utilizing an on-column injector on the chromographic column and housing the column in an oven, the method comprising the steps of:
   (a) maintaining the oven temperature at least 50° C. above the boiling point of the solvent;
   (b) cooling the sample and solvent while the sample and solvent are being injected by cooling the column along a cooling portion of the length thereof wherein the temperature is maintained during the cooling step so as to maintain the solvent and samples in the cooling portion of the column, and the length of the cooling portion is at least 10 cm;
   (c) selecting the quantity of the sample and solvent in accordance with the uncooled length of the precolumn; and
   (d) stopping the cooling step after the solvent and sample have passed through the cooled portion of the column.

20. The method of claim 19, wherein the amount of the sample selected is in the range of 0.1–0.2 $\mu$l per centimeter of the cooling portions length.

21. The method according to 19 wherein the column includes a precolumn portion along which the cooling portion extends.

* * * * *